(12) United States Patent
Domon et al.

(10) Patent No.: US 8,501,942 B2
(45) Date of Patent: Aug. 6, 2013

(54) POLYMERIZABLE MONOMERS

(75) Inventors: Daisuke Domon, Joetsu (JP); Satoshi Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 16 days.

(21) Appl. No.: 13/190,689

(22) Filed: Jul. 26, 2011

(65) Prior Publication Data
US 2012/0029193 A1 Feb. 2, 2012

(30) Foreign Application Priority Data

Jul. 28, 2010 (JP) ................. 2010-169480

(51) Int. Cl.
*C07D 239/02* (2006.01)

(52) U.S. Cl.
USPC .......................................... 544/318

(58) Field of Classification Search
USPC .......................................... 544/318
See application file for complete search history.

(56) References Cited

U.S. PATENT DOCUMENTS

| 5,618,892 | A | 4/1997 | Furihata et al. |
| 6,074,801 | A | 6/2000 | Iwasa et al. |
| 6,437,052 | B1 | 8/2002 | Iwasa et al. |
| 7,037,638 | B1 | 5/2006 | Afzali-Ardakani et al. |
| 2006/0166133 | A1 | 7/2006 | Koitabashi et al. |
| 2008/0241751 | A1 | 10/2008 | Takeda et al. |
| 2009/0142698 | A1 | 6/2009 | Iwashita et al. |

FOREIGN PATENT DOCUMENTS

| CN | 1825206 A | 8/2006 |
| EP | 1684118 A1 | 7/2006 |
| JP | 5-45879 A | 2/1993 |
| JP | 8-202037 A | 8/1996 |
| JP | 2001-226430 A | 8/2001 |
| JP | 2002-49152 A | 2/2002 |
| JP | 2006-201532 A | 8/2006 |
| JP | 2006-215180 A | 8/2006 |
| JP | 2008-249762 A | 10/2008 |

OTHER PUBLICATIONS

Roberto Ballini et al., "TBD-catalysed solventless synthesis of symmetrically N,N'-substituted ureas from primary amines and diethyl carbonate", Royal Society of Chemistry, Green Chemistry, 2003, vol. 5, pp. 396-398.
European Search Report dated Oct. 10, 2011, issued in corresponding European Patent Application No. 11175289.5.

*Primary Examiner* — Yong Chu
*Assistant Examiner* — Valerie Rodriguez-Garcia
(74) *Attorney, Agent, or Firm* — Westerman, Hattori, Daniels & Adrian, LLP

(57) ABSTRACT

A monomer of formula (1) is provided wherein $R^1$ is hydrogen or a monovalent $C_1$-$C_6$ hydrocarbon group, and $R^2$ is a group having polymerization functionality. Using the monomer, crosslinking units can be incorporated into a polymer chain. A chemically amplified negative resist composition comprising a base polymer having crosslinking units incorporated therein has a high sensitivity and forms a resist pattern with minimized LER.

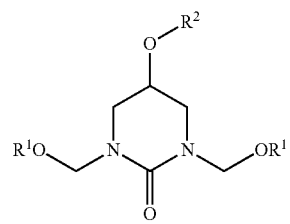

(1)

2 Claims, No Drawings

POLYMERIZABLE MONOMERS

CROSS-REFERENCE TO RELATED APPLICATION

This non-provisional application claims priority under 35 U.S.C. §119(a) on Patent Application No. 2010-169480 filed in Japan on Jul. 28, 2010, the entire contents of which are hereby incorporated by reference.

TECHNICAL FIELD

This invention relates to a polymerizable monomer for use as one component to form a polymer, and more particularly, to a monomer for providing crosslinkable units when used as one component to form a base polymer in a chemically amplified negative resist composition.

BACKGROUND ART

To meet the recent demand for higher integration in integrated circuits, a finer feature size is required for pattern formation. In forming resist patterns with a feature size of 0.2 μm or less, chemically amplified resist compositions utilizing photo-generated acid as the catalyst are typically used in the art because of high sensitivity and resolution. Often, high-energy radiation such as UV, deep UV, EUV or electron beam (EB) is used as the light source for exposure of these resist compositions. Among others, the EB or EUV lithography is recognized most attractive because ultra-fine patterns are expectable.

Resist compositions include positive ones in which exposed areas are dissolved away and negative ones in which exposed areas are left as a pattern. A suitable composition is selected among them depending on the desired resist pattern. In general, the chemically amplified negative resist composition comprises a polymer which is normally soluble in an aqueous alkaline developer, an acid generator which is decomposed to generate an acid upon exposure to light, and a crosslinker which causes the polymer to crosslink between molecules in the presence of the acid serving as a catalyst, thus rendering the polymer insoluble in the developer. Typically a basic compound is added for controlling the diffusion of the acid generated upon light exposure.

A number of negative resist compositions of the type comprising a polymer which is soluble in an aqueous alkaline developer and includes phenolic units as the alkali-soluble units were developed, especially for the KrF excimer laser lithography. These compositions have not been used in the ArF excimer laser lithography because the phenolic units are not transmissive to exposure light having a wavelength of 150 to 220 nm. Recently, these compositions are recognized attractive again as the negative resist composition for the EB and EUV lithography capable of forming ultra-fine patterns. Exemplary compositions are described in JP-A 2006-201532, JP-A 2006-215180, and JP-A 2008-249762.

CITATION LIST

Patent Document 1: JP-A 2006-201532 (US 20060166133, EP 1684118, CN 1825206)
Patent Document 2: JP-A 2006-215180
Patent Document 3: JP-A 2008-249762
Patent Document 4: JP-A 2002-049152
Patent Document 5: JP-A H08-202037
Patent Document 6: JP-A 2001-226430

DISCLOSURE OF THE INVENTION

One requirement for the performance of resist compositions is to reduce the feature size of the pattern. Many improvements were made in negative resist compositions of the type using hydroxystyrene units typical of phenolic units. As the pattern size becomes as fine as 0.1 μm or less, it becomes more important than ever to reduce the line edge roughness (LER) of a fine pattern. The LER may be improved to some extent by reducing the sensitivity of resist film. However, for the EB lithography which is expected to form an ultra-fine pattern, but takes a long time for image writing as compared with the KrF and ArF lithography, the resist film is rather required to have high sensitivity in order to improve throughputs.

It may also contribute to a reduction of LER to reduce the molecular weight of a base polymer. However, since a negative resist composition is designed such that the exposed region is insolubilized by crosslinking the base polymer to increase its molecular weight, the reduced molecular weight of the base polymer indicates a need for further acceleration of crosslinking reaction. As a result, the resist film is reduced in sensitivity. The throughput of image writing is accordingly reduced.

Many attempts were made to overcome the above-discussed problems of LER and throughput. In an attempt to form a pattern having a line width of 0.1 μm or less using a thin resist film having a thickness of 100 nm or less, few desirable properties are available from a combination of prior art materials. There is a demand for certain improvements.

An object of the invention is to provide a novel polymerizable monomer capable of providing crosslinkable units useful as constituent units of a base polymer which is used to formulate a chemically amplified negative resist composition featuring a reduced LER and high sensitivity.

Heretofore, an attempt was made to use calix-arene and similar materials having a relatively low molecular weight in order to form a finer size pattern at a high accuracy by the lithography of high-energy radiation such as EB or EUV (see Patent Document 4).

However, since conventional negative resist compositions rely on the insolubilizing mechanism that a change of the solubility of a base polymer in alkaline developer is triggered by a change of molecular weight, the reduced molecular weight of the base polymer invites a tradeoff in that the degree of crosslink formation must be increased at the sacrifice of sensitivity.

To solve the tradeoff problem, the inventors tried to previously incorporate crosslinker units into a polymer chain. This makes it easy to increase the molecular weight and to improve the sensitivity of the polymer, as compared with the resist composition to which a crosslinker is separately added. The incorporation of crosslinker units in a polymer chain means the distribution of crosslinker units in the polymer matrix, contributing to a reduction of LER in that crosslinking reaction takes place uniformly upon writing of a fine size pattern.

It is already proposed in Patent Documents 5 and 6 to incorporate crosslinker units into a base polymer. However, problems regarding the conditions for the preparation of the base polymer and the age stability of a resist composition formulated from the base polymer remain unsolved.

Among many candidates, the inventors put a focus on tetraalkoxymethylglycoluril and tetrahydroxymethylglycoluril. The inventors' presumption is that if a compound having a bis-N-alkoxymethylureylene group which is an active crosslinking site of tetraalkoxymethylglycoluril or a bis-N-hydroxymethylureylene group which is an active crosslinking site of tetrahydroxymethylglycoluril and polymerization functionality is synthesized, then it becomes possible to incorporate crosslinking units into a polymer chain and that using the resulting polymer, a chemically amplified negative resist composition which is more useful in practice can be formulated.

The inventors have found that a polymerizable monomer having crosslinking ability represented by the general formula (1) shown below can be easily prepared in high yields, and that a chemically amplified negative resist composition comprising a base polymer comprising recurring units derived from the monomer has a high sensitivity and forms a resist film capable of forming a resist pattern with minimized LER.

Accordingly the invention provides a monomer having the general formula (1):

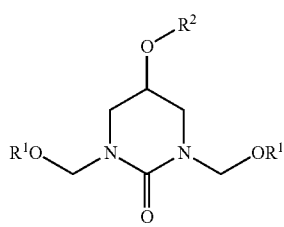

wherein $R^1$ is hydrogen or a monovalent, straight, branched or cyclic hydrocarbon group of 1 to 6 carbon atoms, and $R^2$ is a monovalent group having polymerization functionality.

In a preferred embodiment, $R^2$ is a group having the general formula (2) or (3).

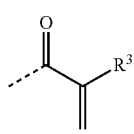

Herein $R^3$ is hydrogen, fluorine, methyl or trifluoromethyl, and the broken line denotes a valence bond to the oxygen atom.

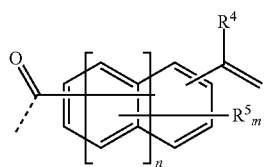

Herein $R^4$ is hydrogen or methyl, $R^5$ is each independently a monovalent, straight, branched or cyclic hydrocarbon group of 1 to 6 carbon atoms which may contain oxygen, or halogen, n is an integer of 0 to 2, m is an integer of 0 to (4+2n), and the broken line denotes a valence bond to the oxygen atom.

Advantageous Effects of Invention

Using the polymerizable monomer, crosslinking units can be easily incorporated into a polymer chain. A resist composition comprising a base polymer having crosslinking units incorporated therein has a high sensitivity and forms a resist pattern with minimized LER.

DESCRIPTION OF EMBODIMENTS

The terms "a" and "an" herein do not denote a limitation of quantity, but rather denote the presence of at least one of the referenced item. As used herein, the notation ($C_n$-$C_m$) means a group containing from n to m carbon atoms per group. The acronym "LER" stands for line edge roughness.

The invention provides a polymerizable monomer having a crosslinking ability, represented by the general formula (1):

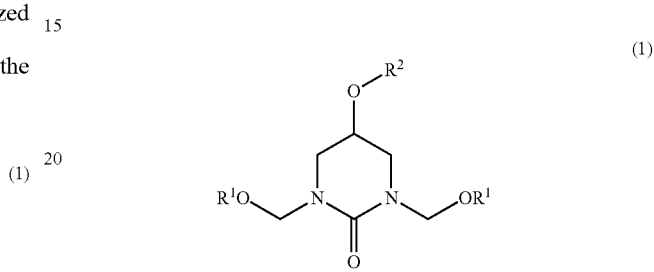

wherein $R^1$ is hydrogen or a monovalent, straight, branched or cyclic hydrocarbon group of 1 to 6 carbon atoms, and $R^2$ is a monovalent group having polymerization functionality.

In formula (1), —$OR^1$ is a functional group which is eliminated under the catalysis of an acid to provide a cation for forming a crosslink. $R^1$ is hydrogen or a monovalent, straight, branched or cyclic hydrocarbon group of 1 to 6 carbon atoms. Examples of the monovalent, straight, branched or cyclic hydrocarbon group include alkyl groups such as methyl, ethyl, propyl, butyl, pentyl, hexyl and structural isomers thereof, cyclopentyl, and cyclohexyl. If $R^1$ is a monovalent hydrocarbon group of more than 6 carbon atoms, a polymer obtained from such a monomer may be less alkali soluble when used in chemically amplified negative resist compositions.

$R^2$ is a monovalent group having polymerization functionality, which is selected from a variety of groups, depending on another monomer for copolymerization and a polymerization technique such as radical polymerization, anionic polymerization or polymerization with transition metal catalysts. While polymers used in resist compositions include, for example, acrylic, styrenic, or norbornene polymers such as cycloolefin/maleic anhydride (COMA) copolymers, polynorbornene and ring-opening metathesis polymerization (ROMP) polymers, a choice may be made of polymerizable functional groups which are applicable to these polymers. In particular, preferred as the functional group for enabling copolymerization with acrylic and styrenic polymers suited for the EB and EUV lithography is a polymerizable group having the following general formula (2) or (3).

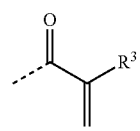

Herein $R^3$ is hydrogen, fluorine, methyl or trifluoromethyl, and the broken line denotes a valence bond to the oxygen atom.

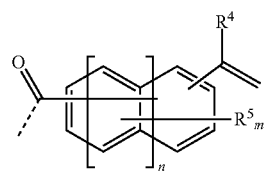

(3)

Herein $R^4$ is hydrogen or methyl, $R^5$ is each independently a monovalent, straight, branched or cyclic hydrocarbon group of 1 to 6 carbon atoms which may contain oxygen, or halogen, n is an integer of 0 to 2, m is an integer of 0 to (4+2n), and the broken line denotes a valence bond to the oxygen atom.

In formula (3), $R^5$ is a monovalent, straight, branched or cyclic $C_1$-$C_6$ hydrocarbon group which may contain oxygen, or halogen. Examples of the monovalent, straight, branched or cyclic $C_1$-$C_6$ hydrocarbon group include alkyl groups such as methyl, ethyl, propyl, butyl, pentyl, hexyl and structural isomers thereof, cyclopentyl, and cyclohexyl. $R^5$ may contain an oxygen atom, and examples of oxygen-containing hydrocarbon groups include alkoxy groups such as methoxy, ethoxy, propoxy, butoxy, pentyloxy, hexyloxy, and structural isomers of hydrocarbon moiety thereof, cyclopentyloxy, cyclohexyloxy. If a monomer has a polymerizable functional group of formula (3) wherein $R^5$ is a monovalent hydrocarbon group of more than 6 carbon atoms, a polymer obtained from the monomer may have too low an alkali solubility for use in chemically amplified negative resist compositions. Exemplary halogen atoms of $R^5$ are fluorine, chlorine, bromine and iodine. By introducing such a group as $R^5$, the alkali solubility, reactivity and other properties of a polymer can be controlled as desired.

Preferred, non-limiting examples of the compound having formula (1) are shown below.

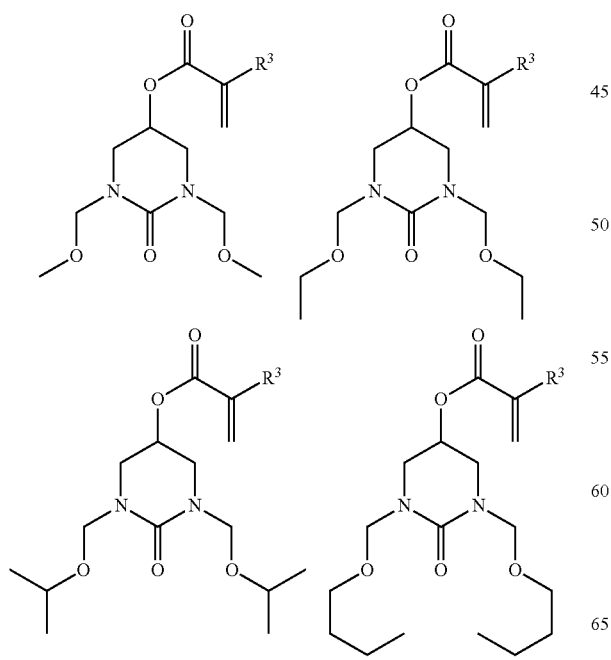

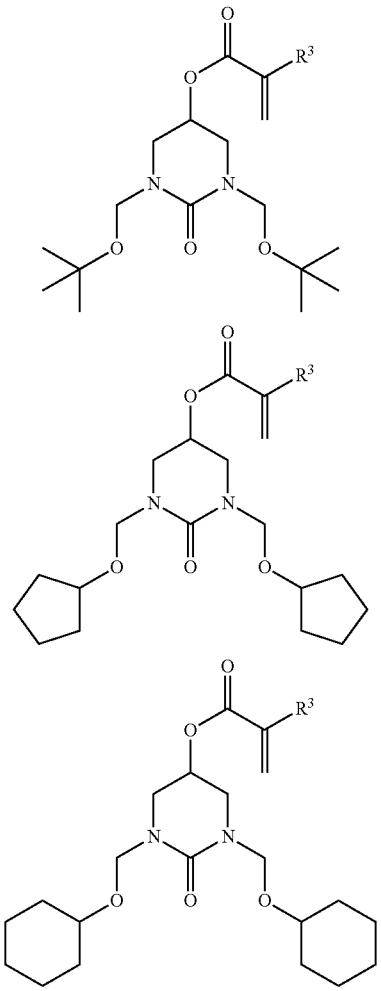

Herein $R^3$ is as defined above.

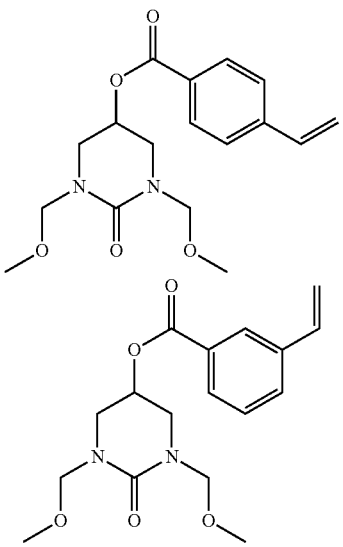

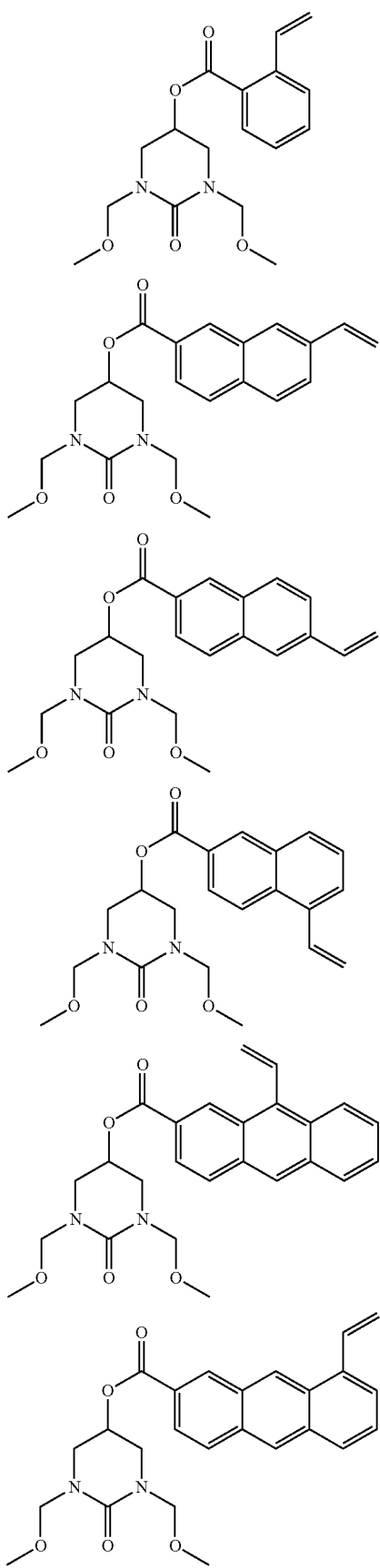

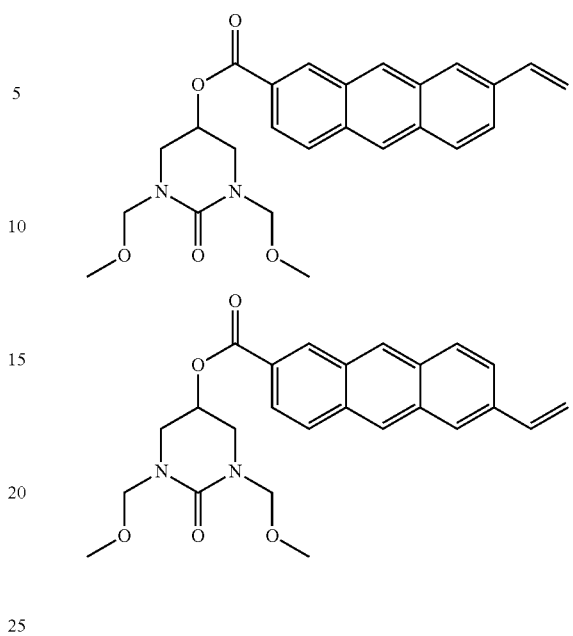

The monomer of formula (1) may be prepared, for example, according to the following scheme A, by forming a compound of formula (6) as an intermediate, and effecting reaction, typically esterification reaction, suitable to utilize a hydroxyl group of the intermediate, thereby forming a bond with a polymerizable unit suitable for use in predetermined polymerization reaction. Specifically, an acrylic monomer of formula (1) may be prepared according to the following scheme A although the method is not limited thereto.

Scheme A

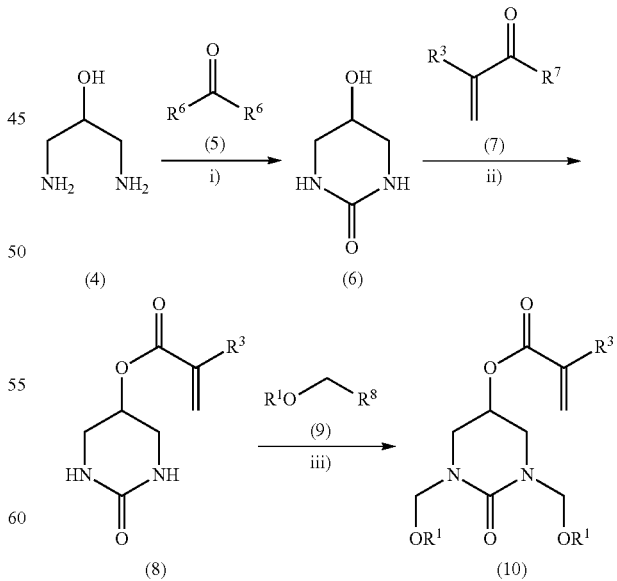

Herein $R^1$ and $R^3$ are as defined above, $R^6$ is methoxy or ethoxy, $R^7$ is halogen or a substituent group of the following formula:

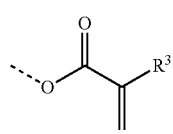

wherein $R^3$ is as defined above, and $R^8$ is halogen.

Scheme A is described in more detail. Step i) is to react 1,3-diamino-2-propanol with a carbonate (5) to form a cyclic urea (6). This reaction may be carried out by the well-known technique (Green Chemistry, Vol. 5, p 396-398, 2003, Royal Society of Chemistry). The reaction may be carried out in a solventless system or in water solvent, by adding 1,3-diamino-2-propanol, carbonate (5), and a base in sequence or at the same time, and optionally cooling or heating. Exemplary of the base are triethylamine, pyridine, 4-dimethylaminopyridine, 1,8-diazabicyclo[5.4.0]undec-7-ene or 1,5,7-triazabicyclo[4.4.0]dec-5-ene. At the end of reaction, the excess carbonate and the solvent were distilled off from the reaction mixture, yielding cyclic urea (6).

Step ii) is to bond a hydroxyl group of cyclic urea (6) with an acryloyl group, which may have a substituent group on double bond, to form an acryloyloxy cyclic urea (8). Reaction may be carried out by a standard technique, preferably by adding cyclic urea (6), acryloyl reagent (7), and a base to a solvent in sequence or at the same time, and optionally cooling or heating. Typical of acryloyl reagent (7) used herein are acid chlorides and acid anhydrides. An amount of acryloyl reagent (7) used is preferably 0.5 to 10 moles, more preferably 1.0 to 5.0 moles per mole of cyclic urea (6).

Examples of the solvent which can be used for the reaction of step ii) include water, ethers such as tetrahydrofuran, diethyl ether, diisopropyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), and N,N-dimethylformamide (DMF), and chlorinated organic solvents such as methylene chloride, chloroform, and carbon tetrachloride. Any suitable solvent may be selected from these solvents depending on other reaction conditions while they may be used alone or in admixture. Examples of the base which can be used for the reaction of step ii) include amines such as ammonia, triethylamine, pyridine, lutidine, collidine, and N,N-dimethylaniline, hydroxides such as sodium hydroxide, potassium hydroxide and tetramethylammonium hydroxide, and carbonates such as potassium carbonate and sodium hydrogen carbonate. The bases may be used alone or in admixture.

The reaction temperature in step ii) is preferably from $-70°$ C. to near the boiling point of the solvent used. An appropriate temperature may be selected depending on other reaction conditions, with a temperature of 0 to 30° C. being most preferred. Since noticeable side reactions like N-acryloyl formation may occur at higher temperatures, it is important for gaining higher yields that reaction be carried out at the permissible lowest temperature at which reaction takes place at a practically acceptable rate. The reaction time is preferably determined as appropriate for gaining higher yields by monitoring the progress of reaction by thin-layer chromatography (TLC) or gas chromatography (GC). Usually the reaction time is about 30 minutes to about 40 hours. The acryloyloxy cyclic urea (8) may be recovered from the reaction mixture by ordinary aqueous work-up. If necessary, the compound may be purified by standard techniques like distillation, recrystallization, and chromatography.

Step iii) is to alkoxymethylate the nitrogen atoms of acryloyloxy cyclic urea (8) to synthesize a crosslinker having a polymerizable functional group (10). Reaction may be carried out by a standard technique, preferably by adding acryloyloxy cyclic urea (8), an alkoxymethyl halide (9), and a base to a solvent in sequence or at the same time, and optionally cooling or heating. An amount of alkoxymethyl halide (9) used is preferably 1.0 to 20 moles, more preferably 2.0 to 10.0 moles per mole of acryloyloxy cyclic urea (8).

Examples of the solvent which can be used for the reaction of step iii) include ethers such as tetrahydrofuran, diethyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), and N,N-dimethylformamide (DMF), and chlorinated organic solvents such as methylene chloride, chloroform, and carbon tetrachloride. Any suitable solvent may be selected from these solvents depending on other reaction conditions while they may be used alone or in admixture. Examples of the base which can be used for the reaction of step iii) include amines such as ammonia, triethylamine, diisopropylethylamine, pyridine, lutidine, collidine, and N,N-dimethylaniline, hydroxides such as sodium hydroxide, potassium hydroxide and tetramethylammonium hydroxide, and carbonates such as potassium carbonate and sodium hydrogen carbonate. The bases may be used alone or in admixture.

The reaction temperature in step iii) is preferably from $-70°$ C. to near the boiling point of the solvent used. An appropriate temperature may be selected depending on other reaction conditions, with a temperature of 0 to 30° C. being most preferred. Since noticeable side reactions may occur at higher temperatures, it is important for gaining higher yields that reaction be carried out at the permissible lowest temperature at which reaction takes place at a practically acceptable rate. The reaction time is preferably determined as appropriate for gaining higher yields by monitoring the progress of reaction by TLC or GC. Usually the reaction time is about 30 minutes to about 40 hours. The crosslinkable monomer (10) may be recovered from the reaction mixture by ordinary aqueous work-up. If necessary, the compound may be purified by standard techniques like distillation, recrystallization, and chromatography.

In order to produce a compound wherein $R^1$ is hydrogen as crosslinker (10) according to the above scheme A, step iii) may be hydroxymethylation, which may be carried out by a well-known technique. Specifically, synthesis from acryloyloxy cyclic urea (8) may be carried out by adding acryloyloxy cyclic urea (8), paraformaldehyde or formalin instead of alkoxymethyl halide (9), and an acid to a solvent in sequence or at the same time, and optionally cooling or heating. An amount of paraformaldehyde or formalin used is preferably 1.0 to 20 moles, more preferably 2.0 to 10.0 moles per mole of acryloyloxy cyclic urea (8).

Examples of the solvent which can be used for the hydroxymethylation reaction of step iii) include ethers such as tetrahydrofuran, diethyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), and N,N-dimethylformamide (DMF), and chlorinated organic solvents such as methylene chloride, chloroform, and carbon tetrachloride. Any suitable solvent may be selected from these solvents depending on other reaction conditions while they may be used alone or in admixture. Examples of the acid which can be used for the hydroxymethylation reaction of step iii) include mineral acids such as hydrochloric acid, sulfuric acid, nitric acid and perchloric acid, and organic acids such as p-toluenesulfonic acid, benzenesulfonic acid and trifluoroacetic acid. These acids may be used alone or in admixture.

The temperature of hydroxymethylation reaction in step iii) is preferably from −70° C. to near the boiling point of the solvent used. An appropriate temperature may be selected depending on other reaction conditions, with a temperature of 0 to 50° C. being most preferred. Since noticeable side reactions may occur at higher temperatures, it is important for gaining higher yields that reaction be carried out at the permissible lowest temperature at which reaction takes place at a practically acceptable rate. The reaction time is preferably determined as appropriate for gaining higher yields by monitoring the progress of reaction by TLC or GC. Usually the reaction time is about 30 minutes to about 40 hours. The crosslinker (10) having a polymerizable functional group wherein $R^1$ is hydrogen may be recovered from the reaction mixture by ordinary aqueous work-up. If necessary, the compound may be purified by standard techniques like distillation, recrystallization, and chromatography.

A polymerizable monomer of formula (1) wherein $R^2$ is a polymerizable functional group of formula (3) may be prepared, for example, according to the following scheme B although the method is not limited thereto.

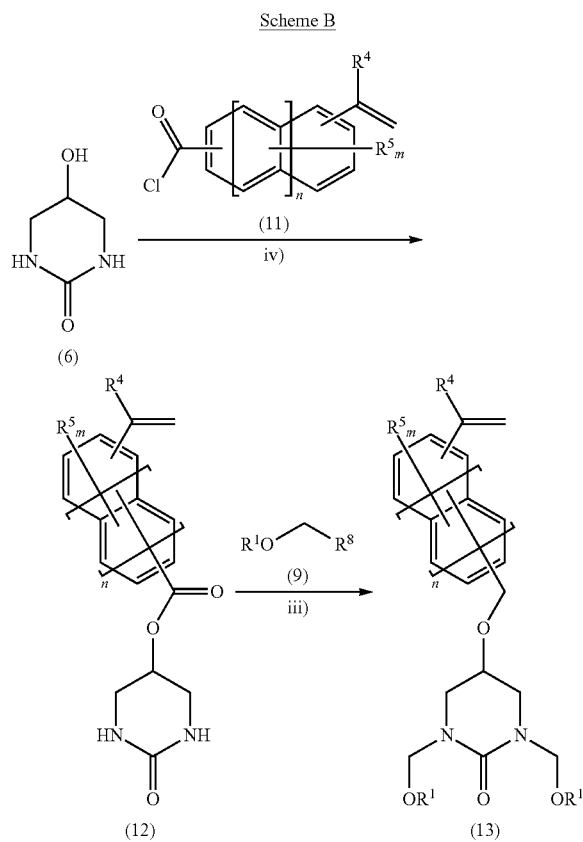

Scheme B

Herein $R^1$, $R^4$, $R^5$, $R^8$, n and m are as defined above.

In Scheme B, step iv) is to couple a hydroxyl group of cyclic urea (6) with a benzoyl group, whose aromatic ring may be substituted, to form a benzoyloxy cyclic urea (12). Reaction may be carried out by a standard technique, preferably by adding cyclic urea (6), a benzoyl reagent (11), and a base to a solvent in sequence or at the same time, and optionally cooling or heating. Typical of benzoyl reagent (11) used herein are acid chlorides and acid anhydrides. An amount of benzoyl reagent (11) used is preferably 0.5 to 10 moles, more preferably 1.0 to 5.0 moles per mole of cyclic urea (6).

Examples of the solvent which can be used for the reaction of step iv) include water, ethers such as tetrahydrofuran, diethyl ether, diisopropyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), and N,N-dimethylformamide (DMF), and chlorinated organic solvents such as methylene chloride, chloroform, and carbon tetrachloride. Any suitable solvent may be selected from these solvents depending on other reaction conditions while they may be used alone or in admixture. Examples of the base which can be used for the reaction of step iv) include amines such as ammonia, triethylamine, pyridine, lutidine, collidine, and N,N-dimethylaniline, hydroxides such as sodium hydroxide, potassium hydroxide and tetramethylammonium hydroxide, and carbonates such as potassium carbonate and sodium hydrogen carbonate. The bases may be used alone or in admixture.

The reaction temperature in step iv) is preferably from −70° C. to near the boiling point of the solvent used. An appropriate temperature may be selected depending on other reaction conditions, with a temperature of 0 to 30° C. being most preferred. Since noticeable side reactions like N-benzoyl formation may occur at higher temperatures, it is important for gaining higher yields that reaction be carried out at the permissible lowest temperature at which reaction takes place at a practically acceptable rate. The reaction time is preferably determined as appropriate for gaining higher yields by monitoring the progress of reaction by TLC or GC. Usually the reaction time is about 30 minutes to about 40 hours. The benzoyloxy cyclic urea (12) may be recovered from the reaction mixture by ordinary aqueous work-up. If necessary, it may be purified by standard techniques like distillation, recrystallization, and chromatography.

Subsequently, a crosslinkable monomer (13) wherein $R^2$ is a group of formula (3) may be produced by subjecting benzoyloxy cyclic urea (12) to the reaction of step iii).

It is understood that monomers suited for various different polymer systems can be synthesized by applying the aforementioned method for monomer synthesis in different ways. For example, if the cyclic urea of formula (6) as the intermediate is combined with norbornenecarboxylic acid chloride, a monomer suited for use in the synthesis of norbornene based polymers is obtainable.

Using the monomer of the invention, a polymer having crosslinking units incorporated therein may be obtained. The resulting polymer is best suited as the base polymer in resist compositions, especially chemically amplified negative resist compositions. The resist composition comprising a polymer having crosslinking units incorporated therein has a high sensitivity and may be processed by lithography to form a pattern having a reduced LER.

EXAMPLE

Examples of the invention are given below by way of illustration and not by way of limitation. The abbreviation "pbw" is parts by weight. For all polymers, a weight average molecular weight (Mw) and a number average molecular weight (Mn) are determined by gel permeation chromatography (GPC) versus polystyrene standards.

Polymerizable monomers having crosslinking ability were synthesized according to the following formulation.

Example 1

Synthesis of 1,3-bismethoxymethyl-2-oxohexahydropyrimidin-5-yl methacrylate (15)

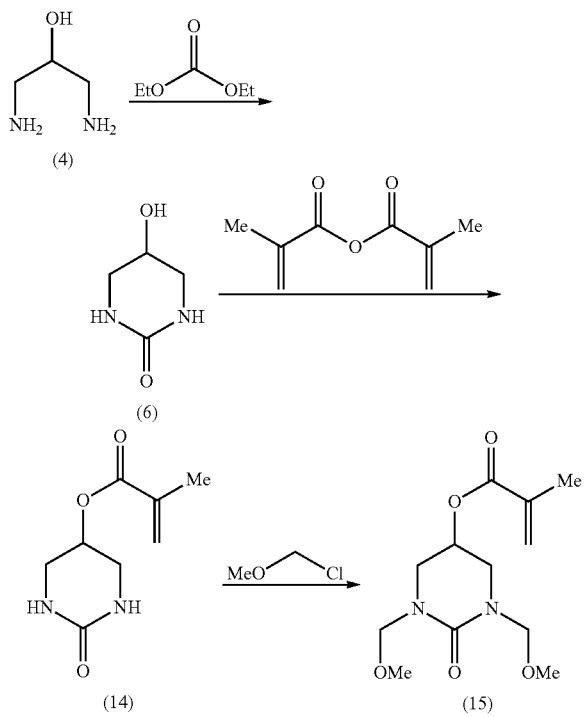

Example 1-1

Synthesis of 5-hydroxytetrahydropyrimidin-2-one (6)

A mixture of 49.1 g of 1,3-diamino-2-propanol (4), 64.4 g of diethyl carbonate, and 3.79 g of 1,5,7-triazabicyclo[4.4.0]dec-5-ene was stirred and heated under reflux for 6 hours. Stirring was continued for a further 10 hours while gradually removing ethanol formed during reaction. Thereafter, the solvent and diethyl carbonate were distilled off in vacuum, obtaining 64.4 g of the end compound, 5-hydroxytetrahydropyrimidin-2-one (6). Yield 100%. The end compound was used in the subsequent step without further purification.

$^1$H-NMR (600 MHz in CDCl$_3$): δ=2.91 (2H, dd), 3.13 (2H, dd), 3.81 (1H, tt), 5.96 (2H, s) ppm.

Example 1-2

Synthesis of 2-oxohexahydropyrimidin-5-yl methacrylate (14)

In a solvent mixture of 45.0 g of tetrahydrofuran (THF) and 36.0 g of H$_2$O was dissolved 9.0 g of 5-hydroxytetrahydropyrimidin-2-one (6) obtained in Example 1-1. To the solution, 17.2 g of methacrylic anhydride and 17.8 g of 25 wt % NaOH aqueous solution were added dropwise below 30° C. Stirring was continued at the temperature for 3 hours, followed by ordinary aqueous work-up. The crude product thus obtained was dissolved in CH$_3$CN and added dropwise to diisopropyl ether, obtaining 8.3 g of the end compound, 2-oxohexahydropyrimidin-5-yl methacrylate (14). Yield 60%.

IR (thin film): ν=3246, 3102, 1682, 1540, 1438, 1299, 1183, 1176, 1146, 1082, 947 cm$^{-1}$ $^1$H-NMR (600 MHz in CDCl$_3$): δ=1.87 (3H, t), 3.18 (2H, dd), 3.37 (2H, dd), 5.00 (1H, t), 5.71 (1H, dq), 6.02 (1H, q), 6.15 (2H, d) ppm.

Example 1-3

Synthesis of 1,3-bismethoxymethyl-2-oxohexahydropyrimidin-5-yl methacrylate (15)

To 80 g of CH$_3$CN were added 5.3 g of diisopropylethylamine, 10.0 g of 2-oxohexahydropyrimidin-5-yl methacrylate (14) obtained in Example 1-2, and 20.0 g of sodium iodide. To the mixture, 11.0 g of chloromethyl methyl ether was added dropwise below 10° C. After the dropwise addition, the reaction mixture was warmed to room temperature and stirred for 5 hours, followed by ordinary aqueous work-up. The product was purified by silica gel column chromatography, obtaining 7.5 g of the target compound, 1,3-bismethoxymethyl-2-oxohexahydropyrimidin-5-yl methacrylate (15). Yield 51%. This is designated Monomer #1.

IR (thin film): ν=2948, 1716, 1645, 1497, 1450, 1388, 1313, 1293, 1214, 1163, 1094, 1069, 1038, 905 cm$^{-1}$ $^1$H-NMR (600 MHz in CDCl$_3$): δ=1.87 (3H, t), 3.14 (3H, s), 3.42 (2H, dd), 3.65 (2H, dd), 4.60 (2H, d), 4.77 (2H, d), 5.20 (1H, dd), 5.71 (1H, q), 6.02 (1H, q) ppm.

Example 2

Synthesis of 1,3-bismethoxymethyl-2-oxohexahydropyrimidin-5-yl 4-vinylbenzoate (17)

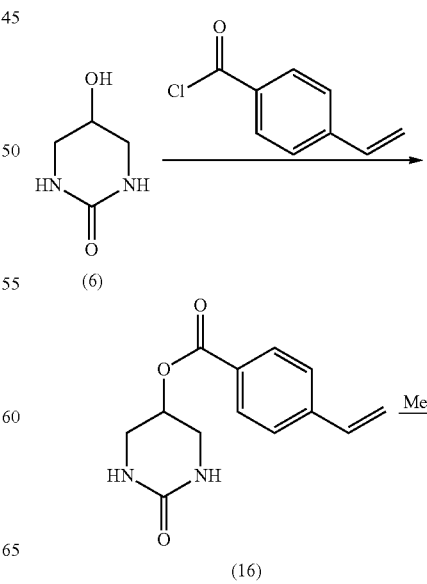

-continued

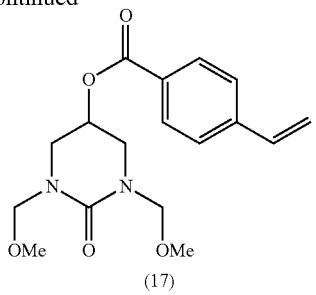

(17)

Example 2-1

Synthesis of 2-oxohexahydropyrimidin-5-yl 4-vinylbenzoate (16)

In a solvent mixture of 50.0 g of tetrahydrofuran (THF) and 40.0 g of $H_2O$ was dissolved 10.0 g of 5-hydroxytetrahydropyrimidin-2-one (6) obtained in Example 1-1. To the solution, 21.5 g of 4-vinylbenzoic acid chloride and 20.7 g of 25 wt % NaOH aqueous solution were added dropwise below 30° C. Stirring was continued at the temperature for 3 hours, followed by ordinary aqueous work-up. The crude product thus obtained was dissolved in $CH_3CN$ and added dropwise to diisopropyl ether, obtaining 13.8 g of the end compound, 2-oxohexahydropyrimidin-5-yl 4-vinylbenzoate (16). Yield 65%.

Example 2-2

Synthesis of 1,3-bismethoxymethyl-2-oxohexahydropyrimidin-5-yl 4-vinylbenzoate (17)

To 84.0 g of $CH_3CN$ were added 36.2 g of diisopropylethylamine, 13.8 g of 2-oxohexahydropyrimidin-5-yl 4-vinylbenzoate (16) obtained in Example 2-1, and 20.9 g of sodium iodide. To the mixture, 11.3 g of chloromethyl methyl ether was added dropwise below 30° C. Stirring was continued at the temperature for 5 hours, followed by ordinary aqueous work-up. The product was purified by silica gel column chromatography, obtaining 10.3 g of the target compound, 1,3-bismethoxymethyl-2-oxohexahydropyrimidin-5-yl 4-vinylbenzoate (17). Yield 55%. This is designated Monomer #2.

Polymer Synthesis Example 1

In a 250-mL dropping funnel under nitrogen blanket, a solution was prepared by adding 48.2 g of 4-acetoxystyrene, 6.0 g of 4-methylstyrene, 6.5 g of acenaphthylene, 9.3 g of Monomer #1 in Example 1, and 7.8 g of dimethyl 2,2'-azobis (2-methylpropionate) (V601, Wako Pure Chemical Industries, Ltd.) to 82.0 g of toluene as solvent. Under nitrogen blanket, a 1-L polymerization flask was charged with 82.0 g of toluene and heated at 80° C., to which the solution was added dropwise over 4 hours. After the completion of dropwise addition, the reaction solution was stirred for 18 hours for polymerization while maintaining the temperature of 80° C., and then cooled to room temperature. The polymerization solution was added dropwise to 1,000 g of hexane whereupon a copolymer precipitate was collected by filtration. The copolymer thus separated was washed twice with 200 g of a hexane/toluene (10/1) mixture. In a 1-L flask under nitrogen blanket, the copolymer was dissolved in a solvent mixture of 126 g of tetrahydrofuran and 42 g of methanol. 18.1 g of ethanolamine was added to the solution, which was stirred at 60° C. for 5 hours. The reaction solution was concentrated in vacuum and dissolved in 300 g of ethyl acetate. The resulting solution was transferred to a separatory funnel along with 80 g of water and 9.1 g of acetic acid, followed by separatory operation. With the lower layer discarded, the organic layer was combined with 80 g of water and 12.1 g of pyridine and subjected to separatory operation. With the lower layer discarded, the organic layer was subjected to water washing/separation using 80 g of water. The water washing/separation was repeated 5 times in total. More definite phase separation was achieved by adding 20 g of acetone and stirring for some time during the standing period on every separatory operation.

The organic layer resulting from the separatory operation was concentrated and dissolved in 140 g of acetone. The acetone solution was passed through a nylon filter having a pore size of 0.02 μm, and added dropwise to 2,800 g of water for precipitation. The crystalline precipitate was filtered, washed with water, and dried, obtaining 45.0 g of a white polymer. The polymer was analyzed by $^{13}C$-NMR, $^1H$-NMR and GPC, with the analytical data shown below.
Copolymer Composition (Molar Ratio)
 4-hydroxystyrene:4-methylstyrene:acenaphthylene: Monomer #1=72.3:8.6:12.7:6.4
 Mw=3,600
 Mw/Mn=1.72
 This is designated Polymer #1.

Polymer Synthesis Example 2

A polymer was synthesized by the same procedure as Polymer Synthesis Example 1 except that 11.0 g of Monomer #2 was used instead of Monomer #1. The polymer was analyzed by $^{13}C$-NMR, $^1H$-NMR and GPC, with the analytical data shown below.
Copolymer Composition (Molar Ratio)
 4-hydroxystyrene:4-methylstyrene:acenaphthylene: Monomer #2=72.1:9.1:12.2:6.6
 Mw=3,500
 Mw/Mn=1.69
 This is designated Polymer #2.

Polymer Synthesis Example 3

In a 250-mL dropping funnel under nitrogen blanket, a solution was prepared by adding 55.5 g of 4-acetoxystyrene, 7.4 g of 4-methylstyrene, 7.5 g of acenaphthylene, and 8.3 g of dimethyl 2,2'-azobis(2-methylpropionate) (V601, Wako Pure Chemical Industries, Ltd.) to 82.0 g of toluene as solvent. Under nitrogen blanket, a 1-L polymerization flask was charged with 82.0 g of toluene and heated at 80° C., to which the solution was added dropwise over 4 hours. After the completion of dropwise addition, the reaction solution was stirred for 18 hours for polymerization while maintaining the temperature of 80° C., and then cooled to room temperature. The polymerization solution was added dropwise to 1,000 g of hexane whereupon a copolymer precipitate was collected by filtration. The copolymer thus separated was washed twice with 200 g of a hexane/toluene (10/1) mixture. In a 1-L flask under nitrogen blanket, the copolymer was dissolved in a solvent mixture of 126 g of tetrahydrofuran and 42 g of methanol. 20.9 g of ethanolamine was added to the solution, which was stirred at 60° C. for 5 hours. The reaction solution was concentrated in vacuum and dissolved in 300 g of ethyl acetate. The resulting solution was transferred to a separatory funnel along with 80 g of water and 10.5 g of acetic acid, followed by separatory operation. With the lower layer discarded, the organic layer was combined with 80 g of water and 14.0 g of pyridine and subjected to separatory operation. With the lower layer discarded, the organic layer was subjected to water washing/separation using 80 g of water. The water washing/separation was repeated 5 times in total. More definite phase separation was achieved by adding 20 g of acetone and stirring for some time during the standing period on every separatory operation.

The organic layer resulting from the separatory operation was concentrated and dissolved in 140 g of acetone. The acetone solution was passed through a nylon filter having a pore size of 0.02 μm and added dropwise to 2,800 g of water for precipitation. The crystalline precipitate was filtered, washed with water, and dried, obtaining 48.0 g of a white polymer. The polymer was analyzed by $^{13}$C-NMR, $^1$H-NMR and GPC, with the analytical data shown below.

Copolymer Composition (Molar Ratio)
   4-hydroxystyrene:4-methylstyrene:acenaphthylene=77.2:9.7:13.1
   Mw=3,500
   Mw/Mn=1.70
   This is designated Polymer #3.

Reference Examples 1 and 2 and Comparative Reference Example 1

In these Examples, chemically amplified negative resist compositions were prepared from the following components.
Base polymer in Reference Examples:
   Polymers #1 and #2 in Polymer Synthesis Examples 1 and 2
Base polymer in Comparative Reference Example:
   Polymer #3 in Polymer Synthesis Example 3
Acid generator: triphenylsulfonium 2,4,6-triisopropylbenzene-sulfonate
Basic compound or Quencher: tris(2-(methoxymethoxy)ethyl)amine
Surfactant: PF-636 (Omnova Solutions, Inc.)
Solvent A: propylene glycol monomethyl ether acetate (PGMEA)
Solvent B: ethyl lactate (EL)
Crosslinker in Comparative Reference Example: tetramethoxymethylglycoluril (TMGU)

Table 1 shows the formulation of chemically amplified negative resist compositions in Reference Examples 1 and 2 and Comparative Reference Example 1.

TABLE 1

| Formulation (pbw) | Reference Example 1 | Reference Example 2 | Comparative Reference Example 1 |
|---|---|---|---|
| Polymer #1 | 80 | | |
| Polymer #2 | | 80 | |
| Polymer #3 | | | 80 |
| Acid generator | 10 | 10 | 10 |
| Crosslinker | | | 8.2 |
| Quencher | 0.1 | 0.1 | 0.1 |
| Surfactant | 0.07 | 0.07 | 0.07 |
| Solvent A | 800 | 800 | 800 |
| Solvent B | 1,800 | 1,800 | 1,800 |

Each of the chemically amplified negative resist compositions was filtered through a nylon polymer filter having a pore size of 0.04 μm. The resist composition was spin-coated at 1,700 rpm onto a 152-mm square mask blank having a chromium oxynitride film at the outermost surface and pre-baked on a hot plate at 110° C. for 10 minutes to form a resist film of 90 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000 (NuFlare Technology Inc., accelerating voltage 50 kV), post-exposure baked (PEB) at 120° C. for 10 minutes, and spray developed with a 2.38 wt % tetramethylammonium hydroxide aqueous solution, thereby yielding negative patterns (Reference Examples 1 and 2 and Comparative Reference Example 1).

The resist pattern was evaluated as follows. The optimum exposure (Eop or sensitivity) was defined as the exposure dose ($\mu C/cm^2$) which provided a 1:1 resolution at the top and bottom of a 200-nm 1:1 line-and-space pattern. The resolution of the resist was defined as the minimum line width of a line-and-space pattern that could be resolved and separated at the optimum exposure. The profile of the resolved resist pattern was evaluated by observing a cross section thereof under SEM and inspecting for the presence or absence of undercut at the substrate interface. The LER of a 100-nm line-and-space pattern was measured under SEM. Table 2 tabulates the results of resolution, pattern profile in cross section, LER, and EB sensitivity.

TABLE 2

| | Resolution (nm) | Pattern profile | LER (nm) | Sensitivity ($\mu C/cm^2$) |
|---|---|---|---|---|
| Reference Example 1 | 40 | good | 4.1 | 10 |
| Reference Example 2 | 40 | good | 4.2 | 10 |
| Comparative Reference Example 1 | 45 | good | 6.5 | 17 |

The data of Table 2 are first discussed in terms of resolution. The chemically amplified negative resist composition having a crosslinker added thereto (Comparative Reference Example 1) recorded a maximum resolution of 45 nm when a pattern was formed therefrom. The chemically amplified negative resist compositions comprising a polymer having a crosslinker incorporated in the polymer chain (Reference Examples 1 and 2) both recorded a maximum resolution of 40 nm, with no substantial difference being observed for whatever type of crosslinker. With respect to the cross-sectional profile of pattern, the resist compositions using any polymers formed rectangular patterns free of bridges and undercuts.

With respect to LER, the chemically amplified negative resist compositions of Reference Examples 1 and 2 showed smaller values of LER than the chemically amplified negative resist composition of Comparative Reference Example 1. This is because diffusion is controlled due to crosslinking units incorporated into the polymer.

With respect to EB sensitivity, the chemically amplified negative resist compositions of Reference Examples 1 and 2 showed a higher sensitivity than the chemically amplified negative resist composition of Comparative Reference Example 1, despite a lower proportion of crosslinking units available. This is because a polymer having crosslinking units incorporated in the polymer chain is easy to increase a molecular weight.

As described above, a chemically amplified negative resist composition comprising a polymer obtained from the monomer of the invention may be used to form a resist film having a high sensitivity and a high writing throughput, which may be processed to form a pattern having a minimized LER. The pattern forming process using the composition is useful in the photolithography for the fabrication of microelectronic components and especially photomask blanks.

Japanese Patent Application No. 2010-169480 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monomer of formula (1):

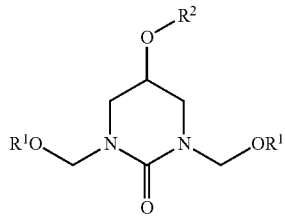

(1)

wherein $R^1$ is hydrogen or a monovalent, straight, branched or cyclic hydrocarbon group of 1 to 6 carbon atoms, and $R^2$ is a monovalent group having polymerization functionality.

2. The monomer of claim 1 wherein $R^2$ is a group of formula (2) or (3):

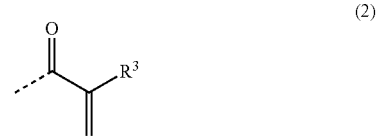

(2)

wherein $R^3$ is hydrogen, fluorine, methyl or trifluoromethyl, and the broken line denotes a valence bond to the oxygen atom,

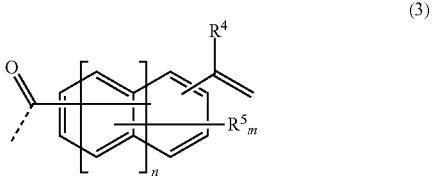

(3)

wherein $R^4$ is hydrogen or methyl, $R^5$ is each independently a monovalent, straight, branched or cyclic hydrocarbon group of 1 to 6 carbon atoms which may contain oxygen, or halogen, n is an integer of 0 to 2, m is an integer of 0 to (4+2n), and the broken line denotes a valence bond to the oxygen atom.

* * * * *